US012027068B2

(12) United States Patent
Mihai et al.

(10) Patent No.: US 12,027,068 B2
(45) Date of Patent: *Jul. 2, 2024

(54) METHOD AND SYSTEMS FOR MODIFYING CONTENT OF AN ELECTRONIC LEARNING SYSTEM FOR VISION DEFICIENT USERS

(71) Applicant: D2L Corporation, Kitchener (CA)

(72) Inventors: Sebastian Mihai, Kitchener (CA); Philip Brown, Kitchener (CA); Chantal Jandard, Kitchener (CA); Mark Cowan, Kitchener (CA)

(73) Assignee: D2L Corporation, Kitchener (CA)

( * ) Notice: Subject to any disclaimer, the term of this patent is extended or adjusted under 35 U.S.C. 154(b) by 1283 days.

This patent is subject to a terminal disclaimer.

(21) Appl. No.: 16/150,840

(22) Filed: Oct. 3, 2018

(65) Prior Publication Data
US 2019/0066526 A1 Feb. 28, 2019

Related U.S. Application Data

(63) Continuation of application No. 14/555,834, filed on Nov. 28, 2014, now Pat. No. 10,102,763.

(51) Int. Cl.
*G09B 5/02* (2006.01)
*A61B 3/06* (2006.01)
(Continued)

(52) U.S. Cl.
CPC ............... *G09B 5/02* (2013.01); *A61B 3/066* (2013.01); *G06F 40/151* (2020.01);
(Continued)

(58) Field of Classification Search
CPC ........ A61B 3/066; G09B 21/008; G09B 5/02; G09B 7/00; G06F 40/151; G06F 40/197; G06T 11/001
See application file for complete search history.

(56) References Cited

U.S. PATENT DOCUMENTS 5,589,898 A * 12/1996 Atkinson ............... A61B 3/066
351/242
6,309,117 B1 * 10/2001 Bunce .................... A61B 3/066
400/61

(Continued)

*Primary Examiner* — Tadesse Hailu
(74) *Attorney, Agent, or Firm* — BERESKIN & PARR LLP/S.E.N.C.R.L., s.r.l.

(57) ABSTRACT

A computer-implemented method for modifying one or more contents of an electronic learning system for a user impaired by a colour vision deficiency. The method includes: generating a vision profile for the user, the vision profile indicating at least a type of the colour vision deficiency, identifying, from the one or more contents, a content to be modified, the content including at least two portions formed of a first colour and a second colour, respectively, the first colour being different from the second colour but the first colour being at least partially indistinguishable from the second colour by the user due to the colour vision deficiency, identifying a content transformation to be applied to the content based on the vision profile, the content transformation including one or more adjustments of the content to accommodate the colour vision deficiency impairing the user; and applying the content transformation to the content.

32 Claims, 10 Drawing Sheets

(51) Int. Cl.
*G06F 40/151* (2020.01)
*G06F 40/197* (2020.01)
*G06T 11/00* (2006.01)
*G09B 7/00* (2006.01)
*G09B 21/00* (2006.01)

(52) U.S. Cl.
CPC .......... *G06F 40/197* (2020.01); *G06T 11/001* (2013.01); *G09B 7/00* (2013.01); *G09B 21/008* (2013.01)

(56) References Cited

U.S. PATENT DOCUMENTS

| | | | | |
|---|---|---|---|---|
| 6,362,830 | B1* | 3/2002 | Walraven | G09G 5/02 345/600 |
| 6,757,428 | B1* | 6/2004 | Lin | G06F 18/256 382/209 |
| 6,985,524 | B1 | 1/2006 | Borchers | |
| 7,272,785 | B2* | 9/2007 | Fukuda | G06F 40/166 707/E17.121 |
| 7,333,117 | B2* | 2/2008 | Kim | H04N 9/68 351/200 |
| 7,737,992 | B2* | 6/2010 | Hong | H04N 9/73 345/603 |
| 10,078,988 | B2* | 9/2018 | Kim | G09G 5/10 |
| 10,102,763 | B2* | 10/2018 | Mihai | A61B 3/066 |
| 10,314,477 | B1* | 6/2019 | Goodsitt | H04N 1/6088 |
| 11,600,197 | B2* | 3/2023 | Anantha | G09B 7/04 |
| 2005/0105796 | A1* | 5/2005 | Hong | H04N 9/73 345/581 |
| 2005/0111019 | A1* | 5/2005 | Nakauchi | G06T 11/001 358/1.9 |
| 2006/0061586 | A1* | 3/2006 | Brulle-Drews | G06F 3/04897 345/594 |
| 2006/0250669 | A1 | 11/2006 | Beretta | |
| 2006/0256127 | A1* | 11/2006 | Cho | A61B 3/066 345/591 |
| 2006/0290712 | A1* | 12/2006 | Hong | H04N 5/14 348/E5.073 |
| 2007/0182755 | A1* | 8/2007 | Jones | G06T 11/001 345/592 |
| 2009/0003578 | A1 | 1/2009 | Jain et al. | |
| 2009/0035733 | A1* | 2/2009 | Meitar | G09B 7/00 434/118 |
| 2009/0066720 | A1* | 3/2009 | Hong | H04N 9/73 345/603 |
| 2009/0128871 | A1* | 5/2009 | Patton | G06T 11/001 382/167 |
| 2009/0263016 | A1* | 10/2009 | Kuo | H04N 1/6027 382/167 |
| 2010/0033679 | A1* | 2/2010 | Kodama | H04N 1/40012 351/242 |
| 2011/0090237 | A1* | 4/2011 | Shimamura | G06T 11/001 345/589 |
| 2012/0147163 | A1* | 6/2012 | Kaminsky | G09G 5/028 345/590 |
| 2012/0299942 | A1* | 11/2012 | Braun | H04N 1/46 345/589 |
| 2013/0083333 | A1* | 4/2013 | Lopez | H04N 1/6088 358/1.9 |
| 2013/0096892 | A1* | 4/2013 | Essa | G09B 7/00 703/2 |
| 2013/0201496 | A1* | 8/2013 | Boggs | G09B 21/008 358/1.9 |
| 2013/0335435 | A1 | 12/2013 | Ambrus et al. | |
| 2014/0122595 | A1* | 5/2014 | Murdoch | C03C 23/006 434/350 |
| 2014/0282285 | A1* | 9/2014 | Sadhvani | G06F 8/38 715/865 |
| 2014/0335497 | A1* | 11/2014 | Gal | G09B 7/00 434/323 |
| 2014/0380154 | A1* | 12/2014 | Solcz | G06T 11/60 715/256 |
| 2015/0072330 | A1* | 3/2015 | Rosenberg | G09B 19/00 434/362 |
| 2015/0120293 | A1* | 4/2015 | Wohlert | G10L 21/10 704/235 |
| 2015/0149902 | A1 | 5/2015 | Zavesky et al. | |
| 2015/0287043 | A1 | 10/2015 | Michaelis et al. | |
| 2015/0287345 | A1 | 10/2015 | Tanuwidjaja | |
| 2016/0132994 | A1* | 5/2016 | Kruglick | G06T 7/20 345/589 |
| 2018/0129518 | A1* | 5/2018 | Lee | G06F 3/14 |
| 2020/0098146 | A1* | 3/2020 | Kuboi | A61B 3/066 |

\* cited by examiner

METHOD AND SYSTEMS FOR MODIFYING CONTENT OF AN ELECTRONIC LEARNING SYSTEM FOR VISION DEFICIENT USERS

RELATED APPLICATIONS

This application is a continuation of U.S. patent application Ser. No. 14/555,834, filed Nov. 28, 2014 now U.S. Pat. No. 10,102,763 and entitled METHODS AND SYSTEMS FOR MODIFYING CONTENT OF AN ELECTRONIC LEARNING SYSTEM FOR VISION DEFICIENT USERS, the entire contents of which are hereby incorporated by reference herein.

TECHNICAL FIELD

The described embodiments relate to methods and systems associated with modifying content of an electronic learning system for vision deficient users and in particular, for users impaired by a colour vision deficiency.

INTRODUCTION

Electronic learning (also known as "e-Learning" or "eLearning") generally refers to education or learning where users engage in education related activities using computers and other computing devices. For example, users may enroll or participate in a course or program of study offered by an educational institution (e.g., a college, university or grade school) through a web interface that is accessible over the Internet. Users may receive assignments electronically, participate in group work and projects by collaborating over the Internet, and be graded based on assignments and examinations that are submitted, for example, using an electronic submission tool.

Electronic learning is not limited to use by educational institutions. Electronic learning may be used in other environments, such as government and corporations. For example, employees at a regional branch office of a corporation may use electronic learning to participate in a training course offered by another office, or even a third-party provider. As a result, the employees at the regional branch office can participate in the training course without having to travel to the site providing the training course. Travel time and costs can be reduced and conserved.

As electronic learning becomes more widespread, the user base increases in diversity and so, the ability to adapt electronic learning systems to accommodate as many types of users as possible becomes increasingly important. For example, certain content, or at least a portion of the content, provided by electronic learning systems may not be viewable by users impaired by a vision deficiency. As a result, those users are prevented from using the electronic learning systems to the fullest extent, or even at all.

BRIEF DESCRIPTION OF THE DRAWINGS

Several embodiments will now be described in detail with reference to the drawings, in which.

Figure 1:
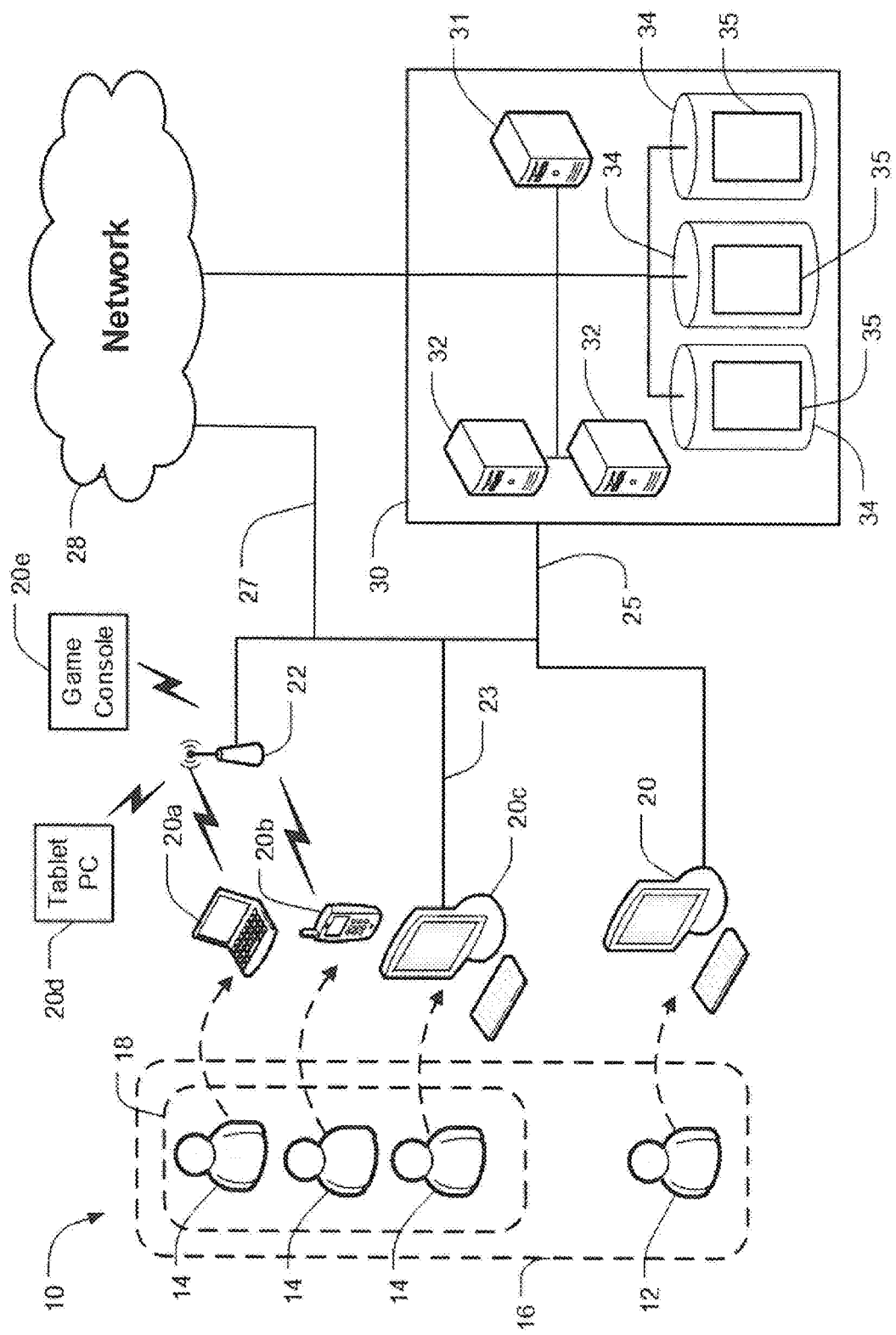
FIG. 1 is a schematic diagram of components interacting with an electronic learning system in accordance with some embodiments.

The drawings, described below, are provided for purposes of illustration, and not of limitation, of the aspects and features of various examples of embodiments described herein.

DESCRIPTION OF SOME EMBODIMENTS

For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments generally described herein. Furthermore, this description is not to be considered as limiting the scope of the embodiments described herein in any way, but rather as merely describing the implementation of various embodiments as described.

The embodiments of the systems and methods described herein may be implemented in hardware or software, or a combination of both. In some cases, embodiments may be implemented in one or more computer programs executing on one or more programmable computing devices comprising at least one processor, a data storage component (including volatile memory or non-volatile memory or other data storage elements or a combination thereof) and at least one communication interface.

For example and without limitation, the programmable computers (referred to below as computing devices) may be a server, network appliance, embedded device, computer expansion module, a personal computer, laptop, personal data assistant, cellular telephone, smart-phone device, tablet computer, a wireless device or any other computing device capable of being configured to carry out the methods described herein.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and combination thereof.

In some embodiments, each program may be implemented in a high level procedural or object-oriented programming and/or scripting language to communicate with a computer system. However, the programs can be implemented in assembly or machine language, if desired. In any case, the language may be a compiled or interpreted language.

Program code may be applied to input data to perform the functions described herein and to generate output information. The output information is applied to one or more output devices, in known fashion.

Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein.

In some embodiments, the systems and methods as described herein may also be implemented as a non-transitory computer-readable storage medium configured with a computer program, wherein the storage medium so configured causes a computer to operate in a specific and predefined manner to perform at least some of the functions as described herein.

Furthermore, the systems, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

The various embodiments described herein generally relate to methods (and associated systems configured to implement the methods) for modifying one or more contents of an electronic learning system. Electronic learning is becoming more widespread and therefore, the ability to adapt electronic learning systems so that they are suitable for use by as many individuals as possible can be critical. For example, individuals impaired by a vision deficiency, such as colour blindness, can sometimes be limited in their use of, or perhaps even prevented from using, electronic learning systems.

Generally speaking, the content described herein includes various types of course content, including for example user generated content as well as other content such as readings, quizzes, examinations assignments, and so on. For instance, some examples of user generated content could include HTML marked-up chat entries in an electronic learning system made by students and/or instructors, HTML marked-up email sent by students and/or instructors, and HTML marked-up discussion posts made by students and/or instructors.

Normal colour vision, for humans, relies on three types of cone cells in the eye. The three types of cone cells are sensitive to three respective spectra of light within the visible light spectrum, resulting in trichromatic colour vision. Colour blindness can involve any degree of deficiency in any one or more of the cone cells so that, as a result, a specific section of the visible light spectrum cannot be perceived. Dichromatic colour vision, for example, is when only two types of cone cells are functional, while monochromatic colour vision is when only one type of cone cell is functional (e.g., mostly black and white vision consisting of different shades of grey).

Red-blindness, or protanopia, is when the red cone cells are absent or not functional. As noted, it is possible that the red cone cells are only reduced in sensitivity, which can be referred to as protanomaly. Generally, individuals with red-blindness perceive the colour red to be darker and tend to confuse black with shades of red; dark brown with dark green, dark orange and dark red; some shades of blue with some shades of red, purples and dark pinks; and mid-greens with some shades of orange.

Green-blindness, or deuteranopia, is when the green cone cells are absent or not functional. Again, it is possible that the green cone cells are only reduced in sensitivity, which can be referred to as deuteranomaly. Generally, individuals with green-blindness confuse shades of mid-red with shades of mid-green or mid-brown; shades of blue-green with grey and shades of mid-pink; shades of bright green with shades of yellow; shades of pale pink with light grey; and shades of light blue with lilac.

Blue-blindness, or tritanopia, is when the blue cone cells are absent or not functional. Again, it is possible that the blue cone cells are only reduced in sensitivity, which can be referred to as tritanomaly. Generally, individuals with blue blindness confuse blue with green, and yellow with violet.

Red-blindness and green-blindness are generally more common than blue-blindness.

Contents provided by the electronic learning systems typically involve some colour. Colour can often help capture, and perhaps retain, a viewer's attention, and may sometimes be incorporated as part of the content. For example, the contents can include images, graphs and text in which colour is a significant component—a pie graph, for instance, can include sectors distinguished by different colours; various portions of a text document can be distinguished by different colours; and images can include components composed of various different colours. Individuals impaired by any degree and type of colour blindness can, therefore, experience difficulties when using electronic learning systems.

Unlike traditional learning environments, such as a classroom setting, providers of the electronic learning systems, as well as content creators and content publishers for the electronic learning systems, are less able to detect, or at least less able to detect within a reasonable amount of time, content users' perception of the content. In traditional learning environments, instructors usually have the opportunity to interact, face-to-face, with the students, and would likely have greater opportunities to detect a vision deficiency impairing the students.

Electronic learning, on the other hand, typically involves at least some self-study by the users before the users submit any work product for review by the content creator, content creator or instructor. A course provided by the electronic learning system, for example, can include multiple modules with a majority of the contents not requiring any response from the user and rather, only for the user to view or read. It is possible that only at the end of a module, or perhaps even at the end of the course, that the user submits any work product or undergoes some form of evaluation related to the course. As a result, when an individual impaired by a vision deficiency participates in the course, some of the contents may not be suitable for the individual. That is, the individual may be unable to perceive the contents in the way that was intended by the content creator due to the vision deficiency. The individual may also not be aware of the discrepancy between how the contents are actually shown by the electronic learning system and how the contents are perceived by the individual. However, even if the individual is, or becomes, aware of the discrepancy and notifies the content provider of the discrepancy, it may be difficult for the content provider to adjust or replace the contents within a reasonable amount of time.

The electronic learning systems described herein can modify the contents for users impaired by a vision deficiency. In order to determine whether any of the contents require modification, the described electronic learning systems can generate a vision profile for each of the users. The vision profile can indicate whether or not a user is impaired by a vision deficiency. In the case that the vision profile indicates that the user is impaired by a vision deficiency, the described electronic learning systems can identify and perform the content transformation necessary for adjusting the content to accommodate the vision deficiency.

The described electronic learning systems may also facilitate creation of the contents by assessing the contents and indicating to the content creator, at the time of creation, that certain contents may be deficient. For an individual impaired by a colour vision deficiency, a content may be deficient if the content contains portions formed of colours that would be at least partially indistinguishable from each other due to the colour vision deficiency. The content creator may then adjust or replace the content accordingly.

Referring now to FIG. 1, illustrated therein is a schematic diagram 10 of components interacting with an electronic learning system 30 for providing electronic learning according to some embodiments.

As shown in the schematic diagram 10, one or more users 12, 14 may access the electronic learning system 30 to participate in, create, and consume electronic learning services, including educational content such as courses. In some cases, the electronic learning system 30 may be part of (or associated with) a traditional "bricks and mortar" educational institution (e.g. a grade school, university or college), another entity that provides educational services (e.g. an online university, a company that specializes in offering training courses, an organization that has a training department, etc.), or may be an independent service provider (e.g. for providing individual electronic learning).

It should be understood that a course is not limited to formal courses offered by formal educational institutions. The course may include any form of learning instruction offered by an entity of any type. For example, the course may be a training seminar at a company for a group of employees or a professional certification program (e.g. Project Management Professional™ (PMP), Certified Management Accountants (CMA), etc.) with a number of intended participants.

In some embodiments, one or more educational groups 16 can be defined to include one or more users 12, 14. For example, as shown in FIG. 1, the users 12, 14 may be grouped together in the educational group 16. The educational group 16 can be associated with a particular course (e.g. History 101 or French 254, etc.), for example. The educational group 16 can include different types of users. A first user 12 can be responsible for organizing and/or teaching the course (e.g. developing lectures, preparing assignments, creating educational content, etc.), such as an instructor or a course moderator. The other users 14 can be consumers of the course content, such as students.

In some examples, the users 12, 14 may be associated with more than one educational group 16 (e.g. some users 14 may be enrolled in more than one course, another example user 12 may be a student enrolled in one course and an instructor responsible for teaching another course, a further example user 12 may be responsible for teaching several courses, and so on).

In some examples, educational sub-groups 18 may also be formed. For example, the users 14 shown in FIG. 1 form an educational sub-group 18. The educational sub-group 18 may be formed in relation to a particular project or assignment (e.g. educational sub-group 18 may be a lab group) or based on other criteria. In some embodiments, due to the nature of electronic learning, the users 14 in a particular educational sub-group 18 may not need to meet in person, but may collaborate together using various tools provided by the electronic learning system 30.

In some embodiments, other educational groups 16 and educational sub-groups 18 could include users 14 that share common interests (e.g. interests in a particular sport), that participate in common activities (e.g. users that are members of a choir or a club), and/or have similar attributes (e.g. users that are male, users under twenty-one years of age, etc.).

Communication between the users 12, 14 and the electronic learning system 30 can occur either directly or indirectly using any one or more suitable computing devices. For example, the user 12 may use a computing device 20 having one or more device processors such as a desktop computer that has at least one input device (e.g. a keyboard and a mouse) and at least one output device (e.g. a display screen and speakers).

The computing device 20 can generally be any suitable device for facilitating communication between the users 12, 14 and the electronic learning system 30. For example, the computing device 20 could be wirelessly coupled to an access point 22 (e.g. a wireless router, a cellular communications tower, etc.), such as a laptop 20a, a wirelessly enabled personal data assistant (PDA) or smart phone 20b, a tablet computer 20d, or a game console 20e. The computing device 20 could be coupled to the access point 22 over a wired connection 23, such as a computer terminal 20c.

The computing devices 20 may communicate with the electronic learning system 30 via any suitable communication channels.

The computing devices 20 may be any networked device operable to connect to the network 28. A networked device is a device capable of communicating with other devices through a network, such as the network 28. A network device may couple to the network 28 through a wired or wireless connection.

As noted, these computing devices may include at least a processor and memory, and may be an electronic tablet device, a personal computer, workstation, server, portable computer, mobile device, personal digital assistant, laptop, smart phone, WAP phone, an interactive television, video display terminals, gaming consoles, and portable electronic devices or any combination of these. These computing devices may be handheld and/or wearable by the user.

In some embodiments, these computing devices may be a laptop 20a, or a smartphone device 20b equipped with a network adapter for connecting to the Internet. In some embodiments, the connection request initiated from the computing devices 20a, 20b may be initiated from a web browser and directed at the browser-based communications application on the electronic learning system 30.

For example, the computing devices 20 may communicate with the electronic learning system 30 via the network 28. The network 28 may include a local area network (LAN) (e.g., an intranet) and/or an external network (e.g., the Internet). For example, the computing devices 20 may access the network 28 by using a browser application provided on the computing device 20 to access one or more web pages presented over the Internet via a data connection 27.

The network 28 may be any network capable of carrying data, including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these, capable of interfacing with, and enabling communication between the computing devices 20 and the electronic learning system 30, for example.

In some examples, the electronic learning system 30 may authenticate an identity of one or more of the users 12, 14 prior to granting the user 12, 14 access to the electronic learning system 30. For example, the electronic learning system 30 may require the users 12, 14 to provide identifying information (e.g., a login name and/or a password) in order to gain access to the electronic learning system 30.

In some examples, the electronic learning system 30 may allow certain users 12, 14, such as guest users, access to the electronic learning system 30 without requiring authentication information to be provided by those guest users. Such guest users may be provided with limited access, such as the ability to review one or more components of the course to decide whether they would like to participate in the course but without the ability to post comments or upload electronic files.

In some embodiments, the electronic learning system 30 may communicate with the access point 22 via a data connection 25 established over the LAN. Alternatively, the electronic learning system 30 may communicate with the access point 22 via the Internet or another external data communications network. For example, one user 14 may use the laptop 20*a* to browse to a webpage (e.g. a course page) that displays elements of the electronic learning system 30.

The electronic learning system 30 can include one or more components for providing electronic learning services. It will be understood that in some embodiments, each of the one or more components may be combined into fewer number of components or may be separated into further components. Furthermore, the one or more components in the electronic learning system 30 may be implemented in software or hardware, or a combination of software and hardware.

For example, the electronic learning system 30 can include one or more processing components, such as computing servers 32. Each computing server 32 can include one or more processor. The processors provided at the computing servers 32 can be referred to as "system processors" while processors provided at computing devices 20 can be referred to as "device processors". The computing servers 32 may be a computing device 20 (e.g. a laptop or personal computer).

It will be understood that although two computing servers 32 are shown in FIG. 1, one or more than two computing servers 32 may be provided. The computing servers 32 may be located locally together, or distributed over a wide geographic area and connected via the network 28.

The system processors may be configured to control the operation of the electronic learning system 30. The system processors can initiate and manage the operations of each of the other components in the electronic learning system 30. The system processor may also determine, based on received data, stored data and/or user preferences, how the electronic learning system 30 may generally operate.

The system processor may be any suitable processors, controllers or digital signal processors that can provide sufficient processing power depending on the configuration, purposes and requirements of the electronic learning system 30. In some embodiments, the system processor can include more than one processor with each processor being configured to perform different dedicated tasks.

In some embodiments, the computing servers 32 can transmit data (e.g. electronic files such as web pages) over the network 28 to the computing devices 20. The data may include electronic files, such as webpages with course information, associated with the electronic learning system 30. Once the data is received at the computing devices 20, the device processors can operate to display the received data.

The electronic learning system 30 may also include one or more data storage components 34 that are in electronic communication with the computing servers 32. The data storage components 34 can include RAM, ROM, one or more hard drives, one or more flash drives or some other suitable data storage elements such as disk drives, etc. The data storage components 34 may include one or more databases, such as a relational database (e.g., a SQL database), for example.

The data storage components 34 can store various data associated with the operation of the electronic learning system 30. For example, course data 35, such as data related to a course's framework, educational content, and/or records of assessments, may be stored at the data storage components 34. The data storage components 34 may also store user data, which includes information associated with the users 12, 14. The user data may include a user profile for each user 12, 14, for example. The user profile may include personal information (e.g., name, gender, age, birthdate, contact information, interests, hobbies, etc.), authentication information to the electronic learning system 30 (e.g., login identifier and password) and educational information (e.g., which courses that user is enrolled in, the user type, course content preferences, etc.).

The data storage components 34 can store authorization criteria that define the actions that may be taken by certain users 12, 14 with respect to the various educational contents provided by the electronic learning system 30. The authorization criteria can define different security levels for different user types. For example, there can be a security level for an instructing user who is responsible for developing an educational course, teaching it, and assessing work product from the student users for that course. The security level for those instructing users, therefore, can include, at least, full editing permissions to associated course content and access to various components for evaluating the students in the relevant courses.

In some embodiments, some of the authorization criteria may be pre-defined. For example, the authorization criteria can be defined by administrators so that the authorization criteria are consistent for the electronic learning system 30, as a whole. In some further embodiments, the electronic learning system 30 may allow certain users, such as instructors, to vary the pre-defined authorization criteria for certain course contents.

The electronic learning system 30 can also include one or more backup servers 31. The backup server can store a duplicate of some or all of the data 35 stored on the data storage components 34. The backup server 31 may be desirable for disaster recovery (e.g. to prevent data loss in the case of an event such as a fire, flooding, or theft). It should be understood that although only one backup server 31 is shown in FIG. 1, one or more backup servers 31 may be provided in the electronic learning system 30. The one or more backup servers 31 can also be provided at the same geographical location as the electronic learning system 30, or one or more different geographical locations.

The electronic learning system 30 can include other components for providing the electronic learning services. For example, the electronic learning system 30 can include a management component that allows users 12, 14 to add and/or drop courses and a communication component that enables communication between the users 12, 14 (e.g., a chat software, etc.). The communication component may also enable the electronic learning system 30 to benefit from tools provided by third-party vendors. Other example components will be described with reference to FIG. 2.

Figure 2:
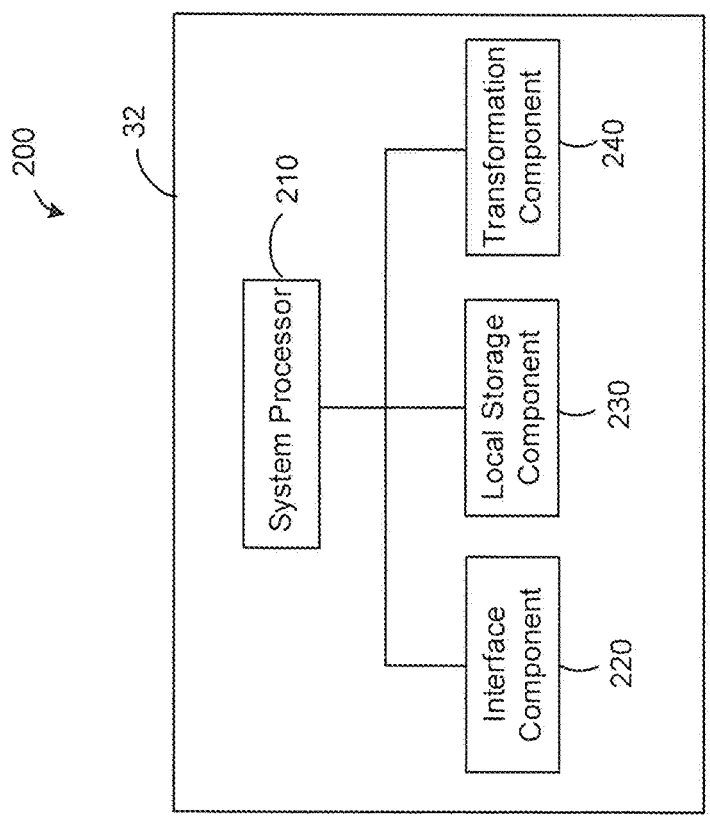
FIG. 2 is a block diagram of some components that may be implemented in the electronic learning system in accordance with an example embodiment.

Referring now to FIG. 2, which is a block diagram 200 of some components that may be implemented in the electronic learning system 30 according to some embodiments. In the example of FIG. 2, the various illustrated components are provided at one of the computing servers 32.

As shown in FIG. 2, the computing server 32 may include a system processor 210, an interface component 220, a local storage component 230 and a transformation component 240. Each of the system processor 210, the interface component 220, the local storage component 230 and the transformation component 240 can be in electronic communication with one another. It should be noted that in alternative embodiments, the system processor 210, the interface component 220, the local storage component 230 and the transformation component 240 may be combined or may be separated into further components. Furthermore, the system processor 210, the interface component 220, the local storage component 230 and the transformation component 240 may be implemented using software, hardware or a combination of both software and hardware.

Generally, the system processor 210 controls the operation of the computing server 32 and, as a result, various operations of the electronic learning system 30. For example, the system processor 210 may initiate the transformation component 240 to identify a content transformation to be applied to the content(s) and to apply the content transformation to the respective content(s) provided by the electronic learning system 30 in accordance with the methods described herein. The system processor 210 may also initiate the transformation component 240 to assess the contents to determine whether any of the content(s) are deficient and to advise the content creator accordingly.

The interface component 220 may be any interface that enables the computing server 32 to communicate with the other computing servers 32, backup servers 31 and data storage components 34 within the electronic learning system 30. The interface component 220 may also include any interface that enables the computing server 32 to communicate with third-party systems. In some embodiments, the interface component 220 can include at least one of a serial port, a parallel port or a USB port. The interface component 220 may also include at least one of an Internet, Local Area Network (LAN), Ethernet, Firewire, modem or digital subscriber line connection. Various combinations of these elements may be incorporated within the interface component 220.

In some embodiments, the interface component 220 may receive input from the computing devices 20 via various input components, such as a mouse, a keyboard, a touch screen, a thumbwheel, a track-pad, a track-ball, a card-reader, voice recognition software and the like depending on the requirements and implementation of the electronic learning system 30.

The local storage component 230 may be provided at the computing server 32 for temporary storage of data associated with various operations of the system processor 210. The local storage component 230 may receive data from and/or transmit data to the data storage components 34.

The transformation component 240 can include the software and data associated with the various methods for modifying and assessing content for an electronic learning system 30 as described herein. Example embodiments will now be described with reference to FIGS. 3 to 6B.

Figure 3:
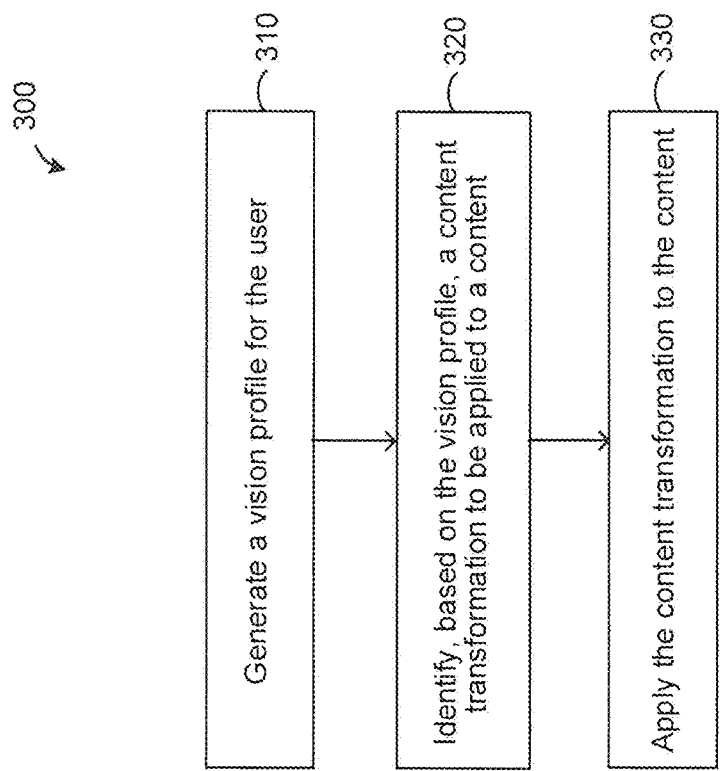
FIG. 3 is a flowchart diagram of an example method for modifying contents of the electronic learning system.

Referring now to FIG. 3, a flowchart diagram illustrating an example method 300 for modifying contents of the electronic learning system 30 is shown. To illustrate the method 300, reference will be made simultaneously to FIGS. 4A to 6B.

At 310, the system processor 210 generates a vision profile for the user.

Generally, as will be described with reference to FIG. 4B, the vision profile can indicate, at least, a vision deficiency that may be impairing the user. For example, the vision profile may indicate a type and/or a degree of colour vision deficiency impairing the user, such as red-blindness or a combination of red-blindness and green-blindness. The degree of vision deficiency may be selected from one of no deficiency, moderately deficient, strongly deficient and absolutely deficient.

The system processor 210 can generate the vision profile by administering a vision test to the user and/or by obtaining inputs from the user associated with his or her vision.

Figure 4A:
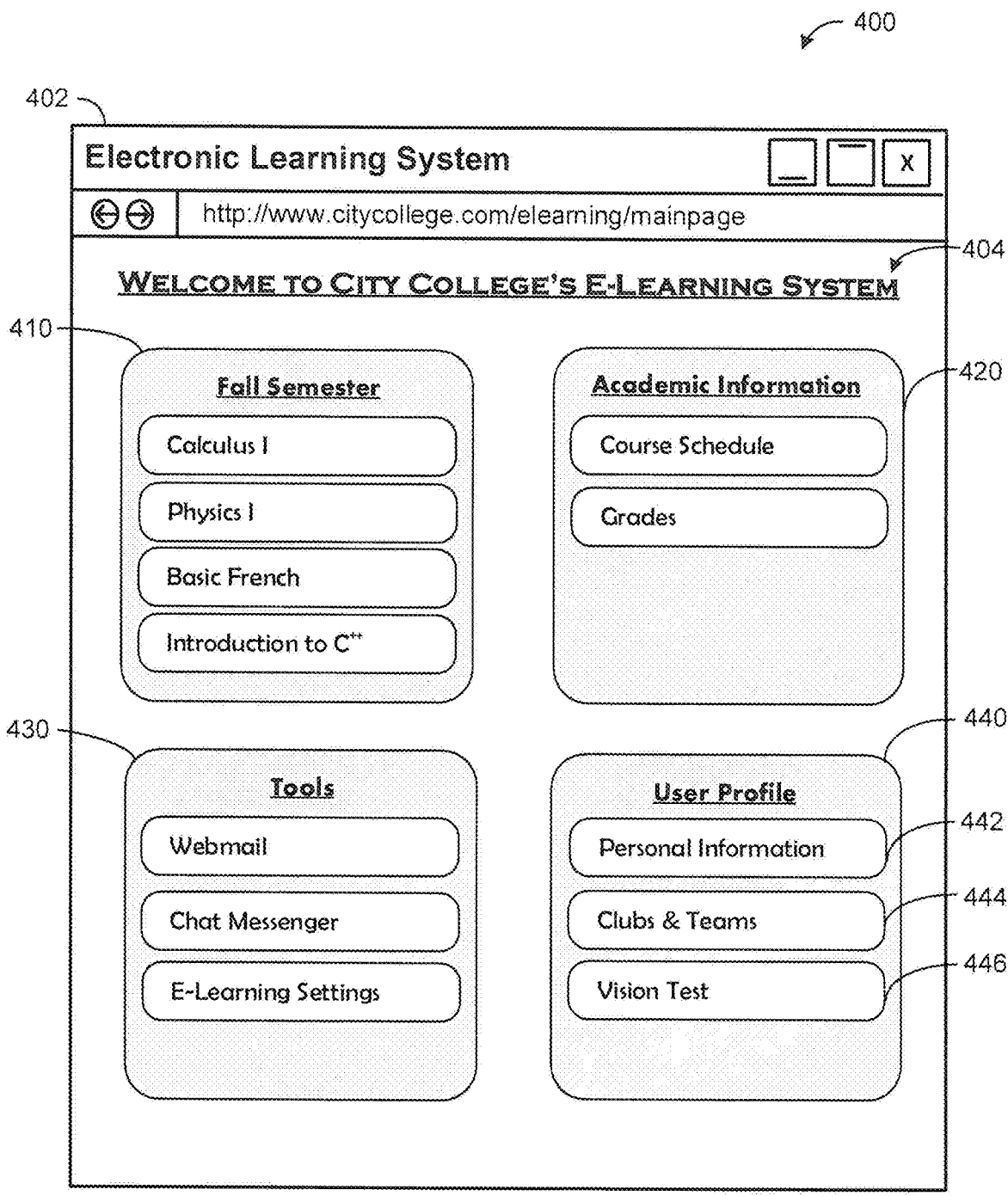
FIG. 4A is a screenshot of an example user interface for the electronic learning system.

FIG. 4A is a screenshot 400 of an example user interface 404 for the electronic learning system 30. The user interface 404 can be provided via a browser application, such as 402.

As shown, the user interface 404 is an example main screen for a user of "City College's" e-learning system. The user interface 404 includes a current semester component 410 (e.g., "Fall" semester component), an academic information component 420, a tools component 430 and a user profile component 440. It will be understood that the user interface 404 is merely an example and that other components may similarly be provided or replace the components shown.

The current semester component 410 can list courses for which the user is registered for that semester. Each of the listed courses may also include a link selectable to provide further details on the respective courses.

The academic information component 420 can include selectable links to data associated with the user's course schedule and grades, for example. Other information relevant to the user's education may be provided.

The tools component 430 can include selectable links to various tools and components. Example tools may include chat software or other messaging components. A settings tool may also be provided in the tools component 430 for varying certain aspects of the electronic learning system for that user.

The user profile component 440 can include selectable links to provide data associated with the user or to collect data from the user. For example, a personal information link 442 can be selected to display a user profile interface 454, such as the example shown in FIG. 4B. An extracurricular activities link 444 can display various information related to clubs and teams that the user is involved in.

A vision test link 446 can be selected to provide one or more vision tests for collecting data from the user for generating a vision profile for the user. In some embodiments, the electronic learning system 30 may administer one or more vision tests automatically when the user initially logs into the system 30.

Various vision tests can be administered to the user via a display of a computing device 20. Example vision tests can include Ishihara tests, Farnsworth Lantern tests, versions of the Ishihara tests and versions of the Farnsworth Lantern tests (e.g., Farnsworth-Munsell 100 hue test), and other related vision perception tests. As is generally known in the art, the Ishihara test and the Farnsworth Lantern test are example colour perception tests for red-blindness and green-blindness.

When generating a vision profile for the user, the electronic learning system 30 may administer multiple different vision tests for each user. The application of multiple different vision tests can help develop a more detailed, and possibly more accurate, vision profile for the user. Based substantially on the results from the various vision tests, the electronic learning system 30 can create the vision profile.

For example, the electronic learning system 30 can determine from the results of an Ishihara test that the user is impaired by relatively strong red-blindness and less than moderate green-blindness, and the electronic learning system 30 can also determine from the results of a Farnsworth Lantern test that the user is impaired by strong red-blindness and moderate green-blindness. The electronic learning system 30 can generate a vision profile for the user by considering the results from both tests. Certain test results may be more reliable for particular types of vision deficiencies, and therefore, the electronic learning system 30 may apply various weights to the test results when generating the vision profile. An example vision profile is shown in FIG. 4B.

The electronic learning system 30 may also store the vision profile in the local storage component 230 and/or the data storage components 34 in association with the user's profile.

Figure 4B:
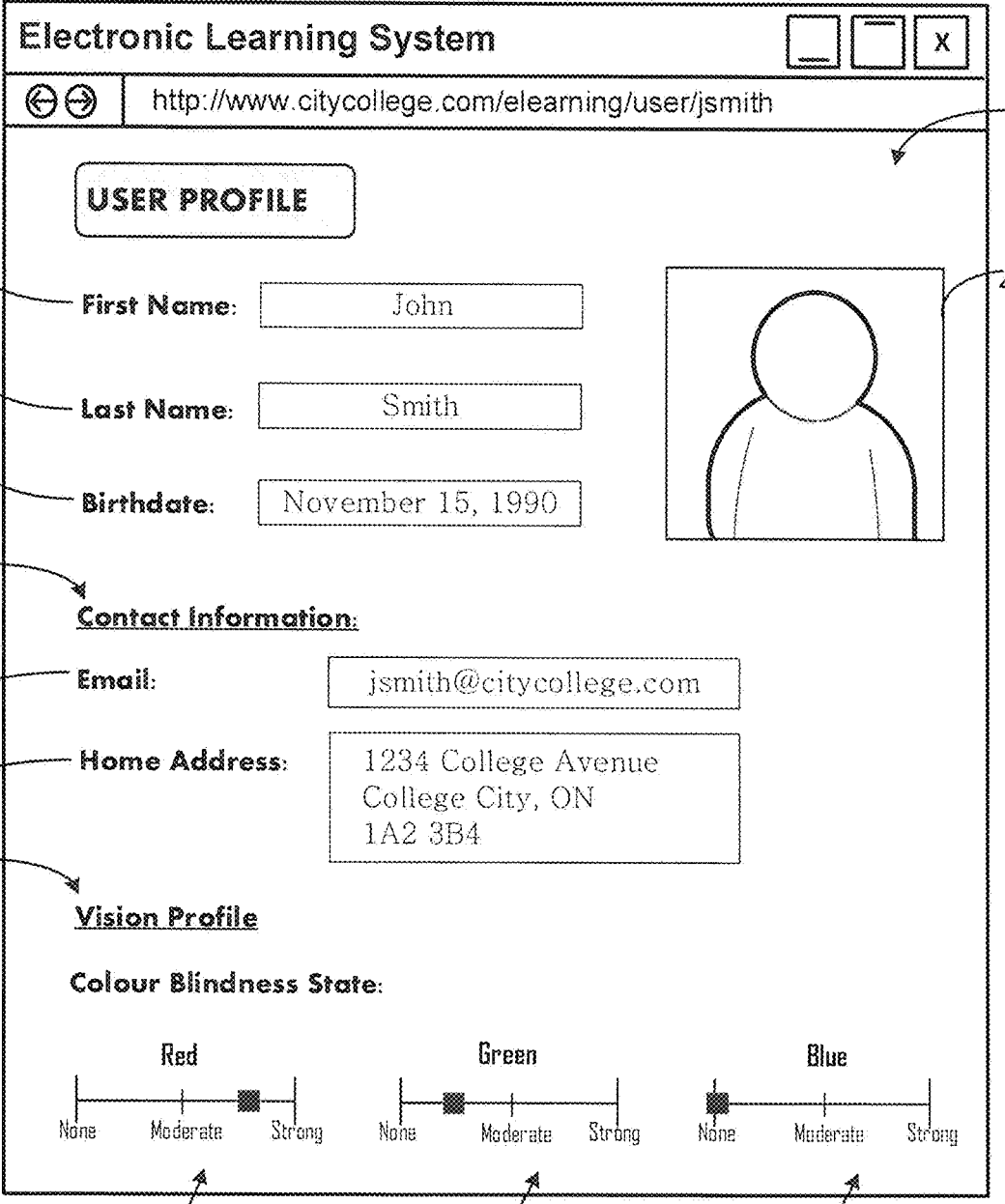
FIG. 4B is a screenshot of an example user profile for a user of the electronic learning system.

Referring now to FIG. 4B, which is a screenshot 450 of an example user profile interface 454. The user profile interface 454 can include various personal information associated with the user, such as a profile image 462, a first name field 464, a last name field 466, a birthdate field 468 and contact information 470 (e.g., an electronic mail address field 472 and a home address field 474). It will be understood that other relevant personal information may similarly be provided in the user profile interface 454.

As shown in the user profile interface 454 for the user, "John Smith", a vision profile 480 is also provided. Continuing with the above example, the vision profile 480 can be generated based on the results from the Ishihara test and the Farnsworth Lantern test administered by the electronic learning system 30. In some embodiments, the electronic learning system 30 may also consider vision information provided by the user apart from the vision tests when generating the vision profile 480. From the vision profile 480, the user "John Smith" is impaired by colour vision deficiency, namely a relatively strong degree of red-blindness (as shown from a red-blindness indicator 482) and a relatively moderate degree of green-blindness (as shown from a green-blindness indicator 484). The severity of the red-blindness and green-blindness is a blend of the results from the Ishihara test and the Farnsworth Lantern test. The user "John Smith" does not appear to be impaired by blue-blindness (as shown from a blue-blindness indicator 486).

Returning to FIG. 3, at 320, the system processor 210 identifies, based on the vision profile 480, a content transformation to be applied to a content.

The content transformation can include adjustments to the content in order to accommodate the vision deficiency impairing the user. For example, for the user "John Smith", the system processor 210 can identify the content transformation needed to adjust the relevant contents to accommodate the relatively strong red-blindness and relatively moderate green-blindness.

When identifying the content transformation, the system processor 210 may also identify contents requiring modification based on the vision profile 480. It may be possible that some contents provided by the electronic learning system 30 may not require modification since they may be viewable by the user despite being impaired by the vision deficiency. For example, contents with only text in one colour unlikely require modification. As a result, processing resources at the electronic learning system 30 can be conserved.

When the vision profile 480 includes a colour vision deficiency, the system processor 210 can identify the content to be modified based on the presence of at least two colours that are at least partially indistinguishable by the user due to the colour vision deficiency. An example content is shown in FIG. 5A.

Figure 5A:
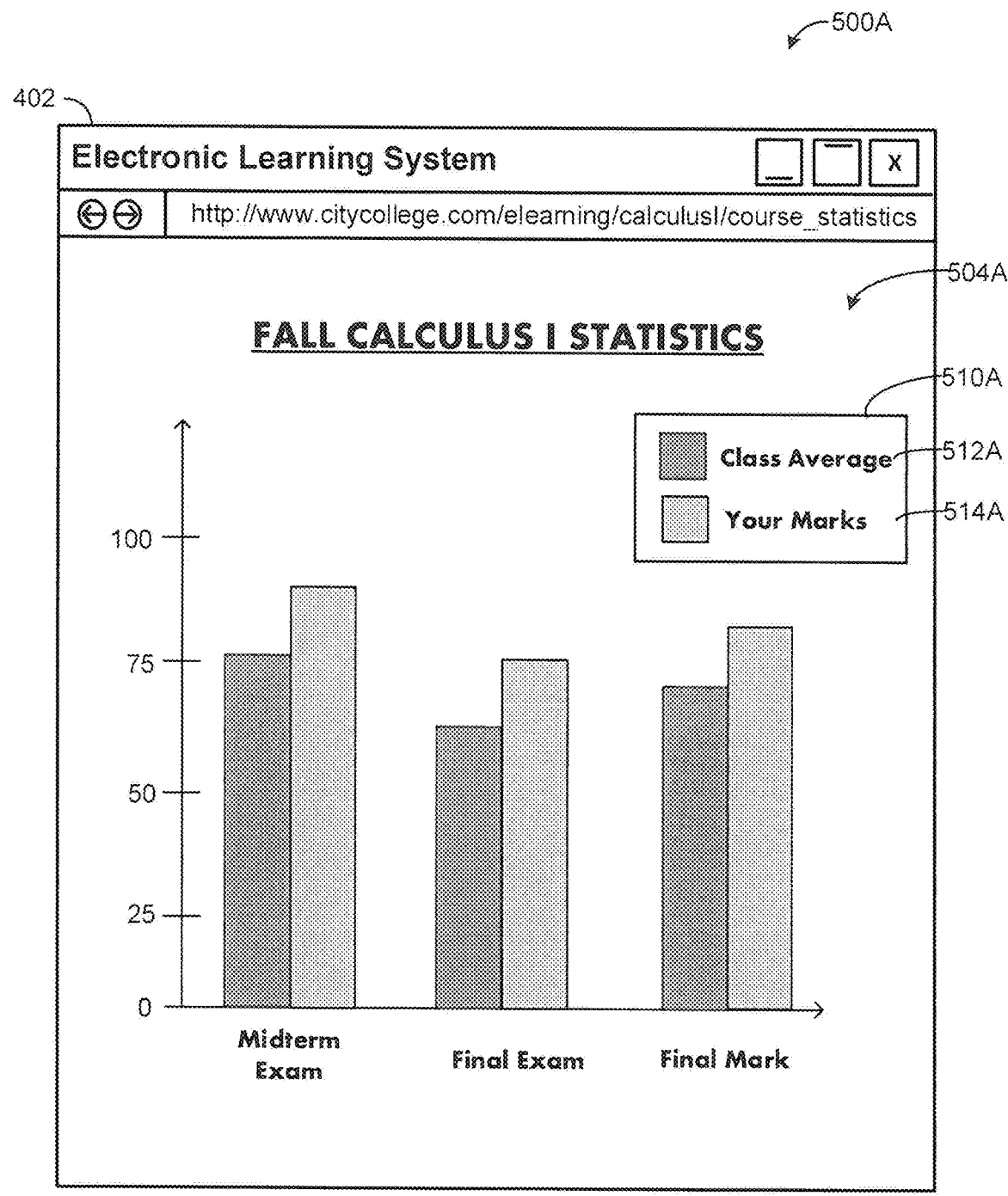
FIG. 5A is a screenshot of a content of the electronic learning system in accordance with an example embodiment.

FIG. 5A is a screenshot 500A of an example content of the electronic learning system 30. The content in FIG. 5A is a graph 504A showing course statistics for a Fall semester of the Calculus I course. The graph 504A is a column graph in which one column depicts a class average and another column depicts the user's marks. The two columns can be distinguished using two different colours (as shown in the legend 510A). In this example, the column associated with the class average is in red (as indicated at 512A in the legend 510A) and the column associated with the user's marks is in green (as indicated at 514A in the legend 510A).

For the graph 504A, the system processor 210 can determine that at least two portions are formed of a first colour (red) and a second colour (green). In some embodiments, the two portions may be neighbouring portions with at least some of the perimeter of one portion being in contact, or at least in very close proximity, with a perimeter of the other portion. Based on the vision profile 480 for "John Smith", the system processor 210 can determine that the first colour (red) is likely to be at least partially indistinguishable from the second colour (green) since the vision profile 480 indicates that "John Smith" is affected by varying degrees of red-blindness and green-blindness.

As described, individuals impaired by red-blindness and green-blindness have absent or non-functional red cone cells and green cone cells, respectively. The portions of the visible light spectrum for which the red cone cell and the green cone cell are responsible overlap, and therefore, individuals affected by red-blindness and green-blindness often perceive colours similarly. In particular, individuals impaired by red-blindness and green-blindness will have difficulty distinguishing between red and green.

Due to the green and red columns, the system processor 210 can, therefore, determine that the graph 504A is a content for which content transformation is to be applied based on the vision profile 480 of the user "John Smith".

The content transformation can vary depending on the vision profile 480. In particular, the severity and the type of the vision deficiency can affect the content transformation to be applied to the content.

In some embodiments, the system processor 210 can identify the content transformation to include replacing the colour(s) with another colour(s). For example, a content transformation for an image with neighbouring portions coloured with different colours that would be at least partially indistinguishable, or perhaps even be perceived as the same colour, by the user can include replacing the colour of one of the neighbouring portions with another colour.

An example colour replacement method can include an edge detection algorithm followed by a flood fill algorithm. It will be understood that other colour replacement methods may similarly be applied. Alternatively, the system processor 210 can adjust the cascading style sheets (CSS) associated with the content.

In respect of the graph 504A in FIG. 5A, the system processor 210 can identify the content transformation to include a replacement of the colour "red" (representing the class average) with a colour more easily distinguishable from the colour "green", such as white perhaps. Alternatively, the system processor 210 can replace green with a colour that is more easily distinguishable from red.

To identify the replacement colour, the system processor 210 may identify a set of colours that can be distinguished by the user based on the vision profile 480. For example, for the user "John Smith", the system processor 210 can determine that since "John Smith" is impaired by varying degrees of red-blindness and green-blindness, the set of replacement colours can include colours outside of the red and green regions of the visible light spectrum. The system processor 210 can then replace the indistinguishable colour with one of the colours in the set of replacement colours.

For less severe vision deficiencies, the system processor 210 may identify content transformation to only include a variation of a contrast of the colour instead of a complete colour replacement. For example, the system processor 210 may vary a portion coloured with light yellow to bright yellow.

In some embodiments, the system processor 210 can identify the content transformation to include replacement of the colours with patterns, or even modification of the content itself. These types of content transformation can be applied for users impaired by very strong vision deficiencies to absolute deficiencies, such as those affected by monochromatic colour vision. An example application of the content transformation involving a replacement of a colour with a pattern will be described with reference to FIG. 5B, and an example application of the content transformation involving a modification of the content will be described with reference to FIGS. 6A and 6B.

Figure 5B:
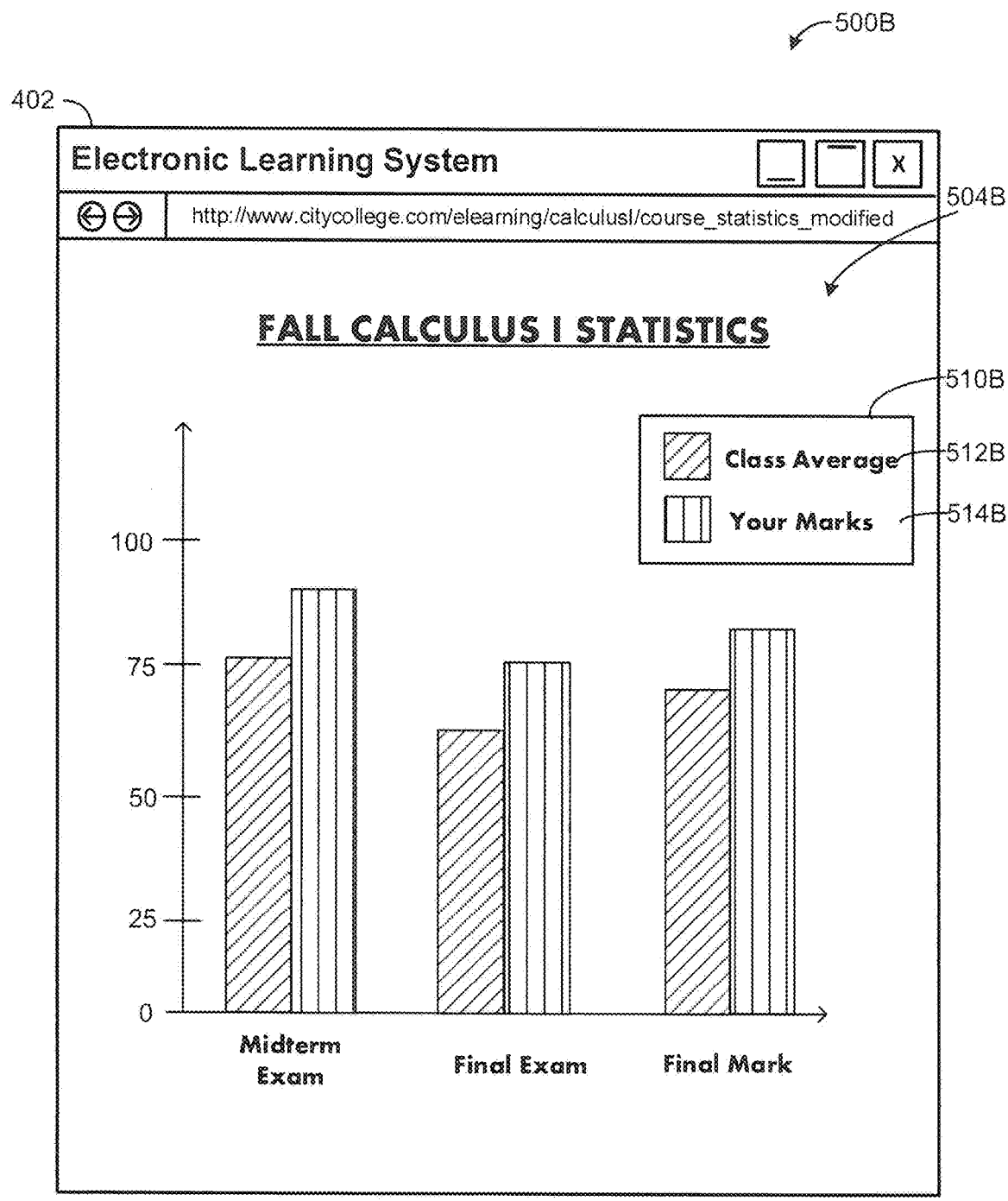
FIG. 5B is a screenshot of a modified version of FIG. 5A in accordance with an example embodiment.

FIG. 5B is a screenshot 500B of a graph 504B modified in accordance with an example embodiment based on the column graph 504A of FIG. 5A. In contrast to the graph 504A, the two columns of the graph 504B are now distinguished using two different patterns (as shown in the legend 510B). The column associated with the class average is in a first pattern (as shown at 512B in the legend 510B) and the column associated with the user's marks is in a second pattern (as shown at 514B in the legend 510B). It will be understood that the patterns can include any variations of dots, lines, etc., that do not involve colours for distinguishing between the different portions of the image. Similar to the example colour replacement method, the pattern replacement method can include an edge detection algorithm followed by replacement of the detected portions with a respective pattern. It will be understood that other pattern replacement methods may similarly be applied.

Figure 6A:
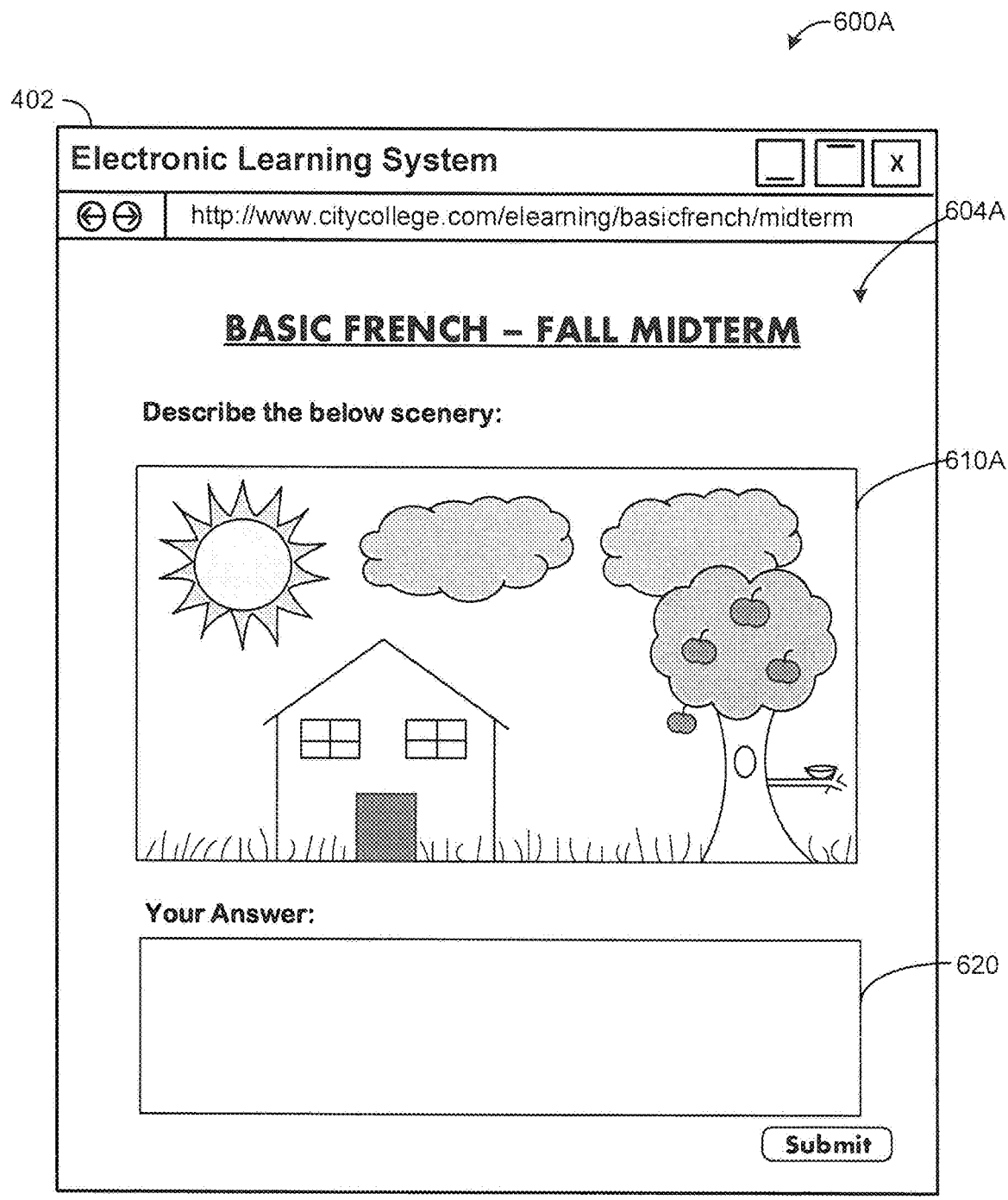
FIG. 6A is a screenshot of another content of the electronic learning system in accordance with an example embodiment.
Figure 6B:
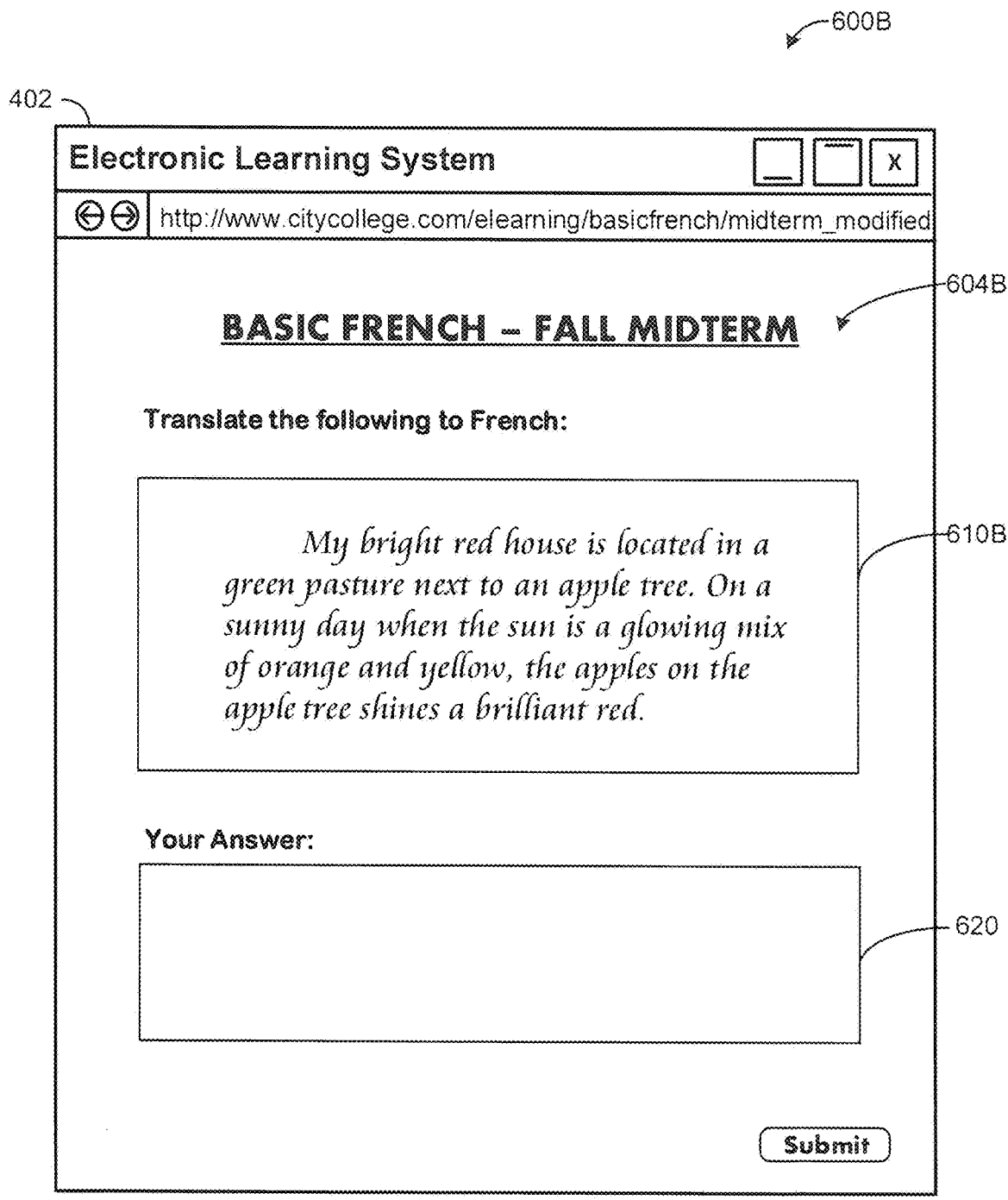
FIG. 6B is a screenshot of a modified version of FIG. 6A in accordance with an example embodiment.

Referring now to FIGS. 6A and 6B, which are screenshots 600A and 600B, respectively, of another example content of the electronic learning system 30.

The content in FIG. 6A is an exam question 604A in a midterm for the course, Basic French. The exam question 604A includes an image 610A and a textbox 620 for receiving a response from the user in respect of the image 610A. The image 610A depicts scenery with the sun in different shades of orange and yellow, clouds in blue, an apple tree with green leaves and red apples, and a house with a brown door. Similar to the graph 504A in FIG. 5A, the system processor 210 can determine from the vision profile 480 that the user "John Smith" would also have difficulties identifying the colours of the various objects in the image 610A due to his colour vision deficiency. To accommodate the vision deficiency, the system processor 210 can, as described, vary the colours in the image 610A. However, due to the importance of the exam question 604A and the relevance of the image 610A on how the user will respond to the exam question 604A, the system processor 210 may instead suggest to the content provider that the image 610A should be modified (or replaced entirely) to ensure that the user "John Smith" can perceive the content in accordance with the content provider's intention.

FIG. 6B shows a modified exam question 604B in which the image 610A of FIG. 6A is now replaced with a text description 610B that generally describes the image 610A. Since the exam question 604A is to evaluate the user's French vocabulary, the modified exam question 604B with the text description 610B can likely evaluate the user's vocabulary in a similar way as the image 610A.

The system processor 210 may also identify the content transformation based on other factors, such as user preferences and/or predefined settings. Certain types of content transformation may be identified by the content provider as being preferred in some situations. For example, the pre-defined settings for a vision profile 480 with strong vision deficiency may involve an aggressive recolouration or pattern replacement for critical contents, such contents used in evaluating a user's knowledge of the course materials. Some users may also indicate certain preferred replacement colours or patterns. It will be understood that other user preferences and settings may similarly be applied.

Returning to FIG. 3, at 330, the system processor 210 applies the content transformation to the content.

Generally, the system processor 210 applies the content transformation to the content before the content is delivered to the browser application 402 (or before it reaches an SMTP server to be sent via email) and is accessed by the user. Emails, chat entries, discussion posts entered by students or instructors may be transformed immediately, in an ad-hoc manner.

The system processor 210 may prioritize when certain contents are to be transformed based on various factors, such as the purpose of the content (e.g., whether the content is purely for decoration or for providing information), an expected access date of the content, and an expected length of time required for transforming the content. It is possible that the system processor 210 may segment the transformation of the contents of a course over time. That is, the system processor 210 can transform the portions of the course that are expected to be accessed first, and continue to transform the other portions over time.

The described electronic learning system 30 may also facilitate creation of the content.

When content creators first develop content for the electronic learning system 30, it may be helpful to identify, upfront, which content may be problematic for users impaired by different vision deficiencies. This can increase the content creator's awareness of how different content is perceived as a result of vision deficiencies and how certain designs of the content should be avoided, if possible.

Figure 7:
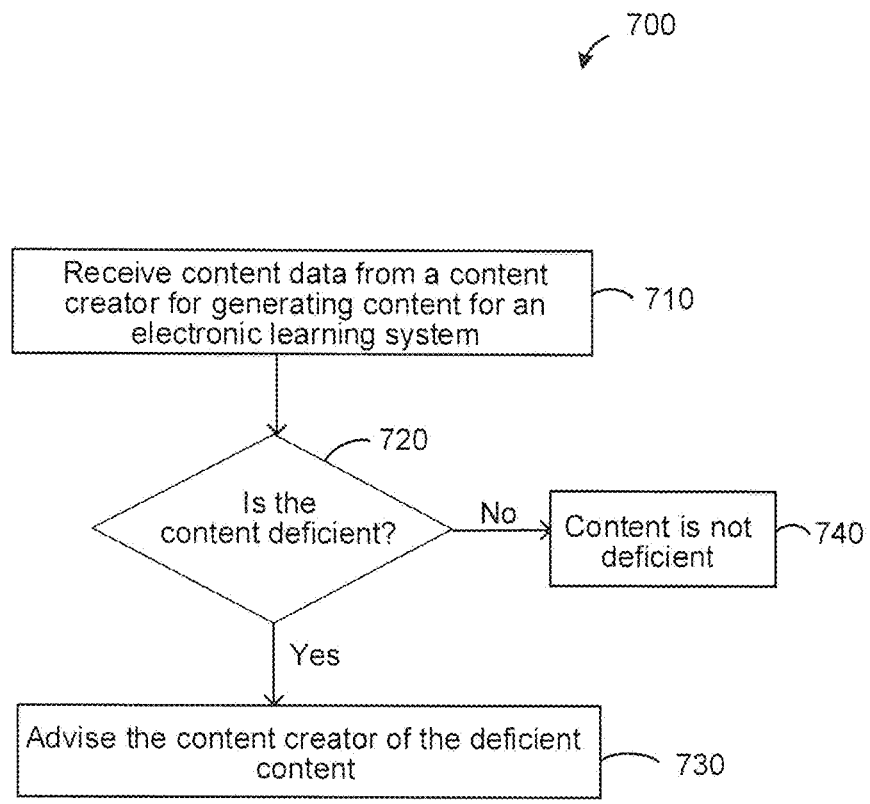
FIG. 7 is a flowchart diagram of an example method for assessing content of the electronic learning system.
Figure 8:
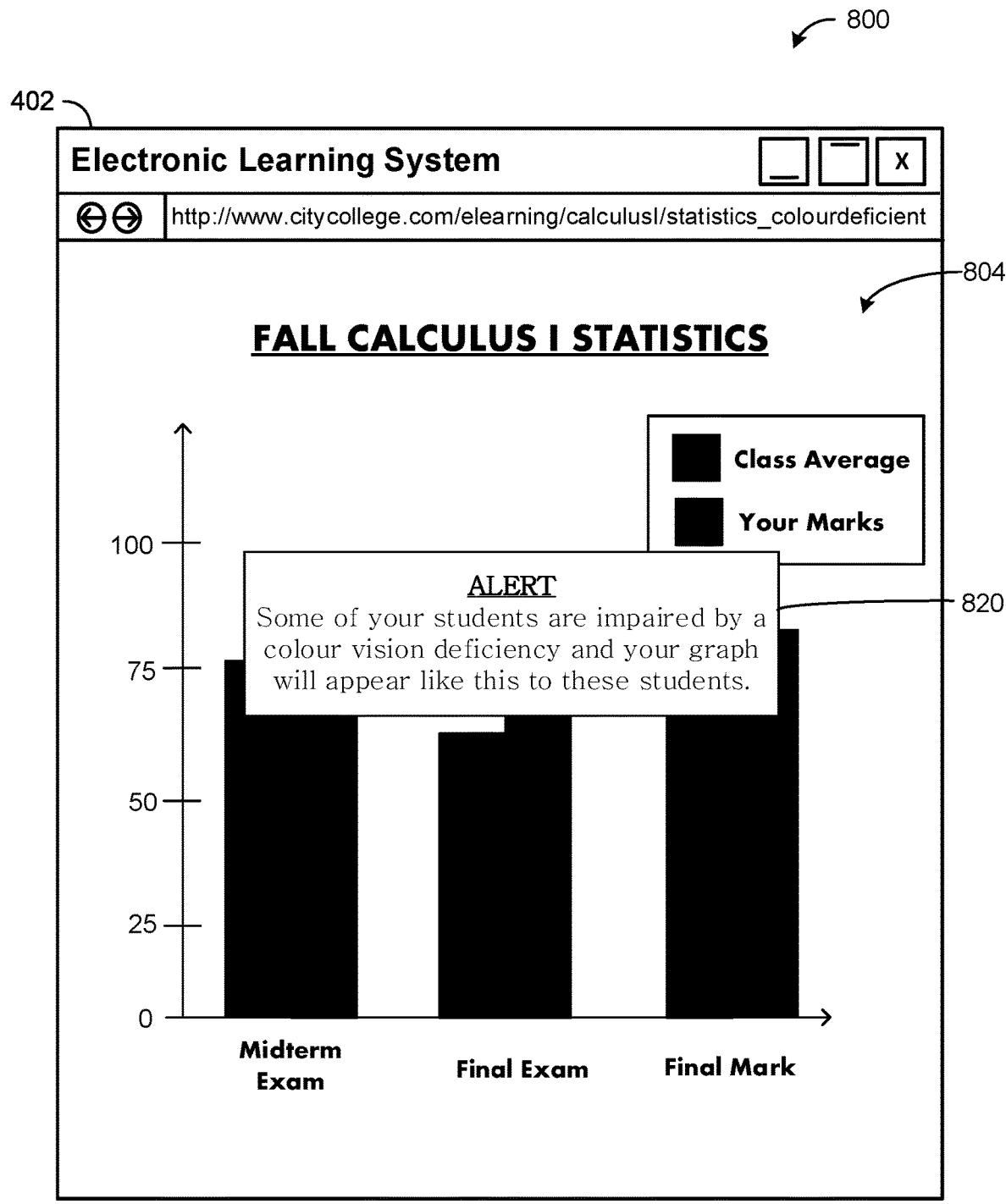
FIG. 8 is a screenshot of another version of FIG. 5A in accordance with another example embodiment.

Referring now to FIG. 7, which is a flowchart diagram illustrating an example method 700 for assessing content for the electronic learning system 30. To illustrate the method 700, reference will be made simultaneously to FIGS. 5A and 8. FIG. 8 is a screenshot 800 of a graph 804, which is another version of the graph 504A of FIG. 5A.

At 710, the system processor 210 receives content data from a content creator for generating content for the electronic learning system 30.

The content data can include any form of data information that can be used to generate the content to be provided by the electronic learning system 30. The content can be course content to be provided to a group of students, such as the educational group 16. Example content data can include images, text information, course statistics, course information, course roster, and other relevant information.

At 720, the system processor 210 determines whether the content is deficient.

The content can be considered deficient when the system processor 210 identifies at least two portions of the content are formed of two colours, respectively, that are at least partially indistinguishable by an individual impaired by a colour vision deficiency. Example methods for identifying the portions of the content with colours that are at least partially indistinguishable due to a vision deficiency are described above with reference to 320 of FIG. 3.

The system processor 210 may, in some embodiments, determine whether any student in the educational group 16 is impaired by a colour vision deficiency and determine whether the content is deficient based on the colour vision deficiency of any of those students. The vision profile 480 for each student may be previously stored in the local storage component 230 or the data storage components 34, and available for retrieval by the system processor 210.

At 730, in response to determining the content is deficient, the system processor 210 advises the content creator of the deficient content.

Continuing with reference to the example shown in FIG. 5A, as described, the system processor 210 can determine, for users impaired by varying degrees of red-blindness and green-blindness, such as the user "John Smith", that the colour (red) representing the class average is likely at least partially indistinguishable from the colour (green) representing "John Smith's" marks. When the graph 504A was being generated, the system processor 210 can detect the problem caused by the colours green and red, and advise the content creator of the deficient content.

When advising the content creator of the deficient content, the system processor 210 may provide a version of the graph 504A as would be perceived by an individual impaired by a vision deficiency, or versions of the graph 504A as would be perceived by individuals impaired by various different vision deficiencies. The modified graph 804 in FIG. 8 illustrates how the graph 504A may be perceived by the user "John Smith" who is impaired by varying degrees of red-blindness and green-blindness. As shown in FIG. 8, "John Smith" is unlikely able to distinguish between the red and green columns. The modified graph 804 also includes an alert 820 explaining the modified graph 804. It will be understood that FIG. 8 is merely an example and that other configurations and designs may similarly be provided.

In some embodiments, the system processor 210 may, in response to detecting a deficient content, offer replacement content for the deficient content. The replacement content may be a version of the deficient content with the indistinguishable colours enhanced, replaced with distinguishable colours, or replaced with patterns. The replacement content may alternatively be an alternative content that the system processor 210 determines to be analogous to the deficient content.

Otherwise, the system processor 210 may indicate, at 740, that the content is not deficient.

The embodiments herein been described here by way of example only. Various modification and variations may be made to these example embodiments. Also, in the various user interfaces illustrated in the figures, it will be understood that the illustrated user interface text and controls are provided as examples only and are not meant to be limiting. Other suitable user interface elements may be possible.

We claim:

1. A computer-implemented method for modifying one or more contents of an electronic learning system for a user impaired by a colour vision deficiency prior to the user accessing the one or more contents, the method comprising:
   receiving, from a computing device associated with the user, inputs associated with a vision of the user;
   generating, at a first hardware processor remote from the computing device, a vision profile for the user based on the inputs, the vision profile indicating the colour vision deficiency of the user, the colour vision deficiency defining of each of a red-blindness, a green-blindness and a blue-blindness of the user;
   determining based on the vision profile, whether at least one content from the one or more contents is to be modified, the content to be modified including at least two portions formed of a first colour and a second colour, respectively, the first colour being different from the second colour but the first colour being at least partially indistinguishable from the second colour by the user due to the colour vision deficiency;
   in response to determining that at least one content is to be modified, identifying a content transformation to be applied to the at least one content based on the vision profile, the content transformation including one or more adjustments of the content to accommodate the colour vision deficiency impairing the user;
   applying the content transformation to the content; and
   transmitting the transformed content to a second hardware processor for displaying the transformed content at a display of the computing device via a network.

2. The method of claim 1, wherein identifying the content transformation to be applied to the content based on the vision profile comprises:
   identifying the one or more adjustments based on the severity level of the type of the colour vision deficiency.

3. The method of any one of claims 1 and 2, wherein the one or more adjustments comprises one of (i) changing the first colour to a different colour, (ii) replacing the first colour with a pattern, and (iii) modifying the content.

4. A system for modifying one or more electronic contents for a user impaired by a colour vision deficiency prior to the user accessing the one or more contents, the one or more electronic contents being provided by an electronic learning system, the system comprising:
- a computing device associated with the user configured to transmit inputs associated with a vision of the user to a hardware processor remote from the computing device via a network; and
- the hardware processor configured to:
  - generate a vision profile for the user based on the inputs, the vision profile indicating the colour vision deficiency, the colour vision deficiency defining a severity level of each of a red-blindness, a green-blindness and a blue-blindness of the user;
  - determine based on the vision profile, whether at least one content from the one or more contents is to be modified, the content to be modified including at least two portions formed of a first colour and a second colour, respectively, the first colour being different from the second colour but the first colour being at least partially indistinguishable from the second colour by the user due to the colour vision deficiency;
  - in response to determining that at least one content is to be modified, identify a content transformation to be applied to the at least one content based on the vision profile, the content transformation including one or more adjustments of the content to accommodate the colour vision deficiency impairing the user;
  - apply the content transformation to the content; and
  - transmit the transformed content via the network to a second hardware processor in communication with the computing device for displaying the transformed content at a display of the computing device.

5. The system of claim 4, wherein the first hardware processor is configured to:
- identify the one or more adjustments based on the severity level of the type of colour vision deficiency.

6. The system of any one of claims 4 and 5, wherein the one or more adjustments comprises one of (i) changing the first colour to a different colour, (ii) replacing the first colour with a pattern, and (iii) modifying the content.

7. A computer-implemented method for modifying one or more contents of an electronic learning system for a user prior to the user accessing the one or more contents, the method comprising:
- receiving, from a computing device associated with the user, inputs associated with a vision of the user;
- generating at a first hardware processor remote from the computing device a vision profile for the user, the vision profile indicating at least a vision deficiency impairing the user and a severity level of the vision deficiency based on the inputs;
- determining whether at least one content of the one or more contents is to be modified based on the vision profile;
- retrieving at least one property of the content to be modified, the at least one property comprising at least a purpose of the content for an electronic learning activity provided by the electronic learning system;
- identifying a content transformation to be applied to the content based on the vision profile, provider preferences, the provider preferences defining content transformation preferences of a provider of the one or more electronic contents and the at least one property of the content, the content transformation including one or more adjustments of the content to accommodate the vision deficiency impairing the user;
- applying the content transformation to the content; and
- transmitting the transformed content via the network to a second hardware processor for displaying the transformed content at a display of the computing device.

8. The method of claim 7, wherein generating the vision profile for the user comprises:
- providing, via the display, a vision test to the user; and
- creating the vision profile based substantially on results of the vision test.

9. The method of claim 8, wherein the vision test comprises at least one or more of a version of an Ishihara test and a version of a Farnsworth Lantern test.

10. The method of any one of claims 7 to 9, wherein identifying the content transformation to be applied to the content of the one or more contents based on the vision profile comprises:
- determining, from the vision profile, the vision deficiency includes a colour vision deficiency; and
- in response to determining the vision deficiency includes the colour vision deficiency, indicating the content transformation includes one of (i) changing at least one colour of the content to a different colour, (ii) replacing the at least one colour of the content with a pattern, and (iii) modifying the content.

11. The method of claim 10;
wherein the content to be modified, includes two neighbouring portions, each portion of the two neighbouring portions being associated with a respective first and second colour, the first colour being different from the second colour but the first colour being at least partially indistinguishable from the second colour by the user due to the vision deficiency indicated in the vision profile.

12. The method of claim 11 further comprises:
- identifying a set of colours distinguishable by the user despite the vision deficiency; and
- changing the first colour to a colour from the set of colours, the colour being different from the second colour.

13. The method of claim 11 further comprises replacing the first colour with a pattern.

14. The method of claim 7, wherein the severity level is selected from one of slightly deficient, moderately deficient, strongly deficient and absolutely deficient.

15. The method of claim 14, further comprises:
- in response to determining the severity level is absolutely deficient, indicating the content transformation includes replacing at least one colour of the content with a pattern.

16. The method of claim 7, wherein the at least one property further comprises at least one of an expected access date of the content and an expected length of time required for transforming the content.

17. A system for modifying one or more electronic contents for a user prior to the user accessing the one or more contents, the one or more electronic contents being provided by an electronic learning system, the system comprising:
- a computing device associated with the user configured to transmit inputs associated with a vision of the user to a hardware processor remote from the computing device via a network;
- the first hardware processor configured to:
  - generate a vision profile for the user, the vision profile indicating at least a vision deficiency impairing the user and a severity level of the vision deficiency based on the inputs;

determine whether at least one content of the one or more contents is to be modified based on the vision profile for the user;

retrieve at least one property of the content to be modified, the at least one property comprising at least a purpose of the content for an electronic learning activity provided by the electronic learning system;

identify a content transformation to be applied to the content based on the vision profile, provider preferences, the provider preferences defining content transformation preferences of a provider of the one or more electronic contents, and the at least one property of the content, the content transformation including one or more adjustments of the content to accommodate the vision deficiency impairing the user;

apply the content transformation to the content;

transmit the transformed content via the network to a second hardware processor in communication with the computing device, for displaying the transformed content at a display of the computing device.

18. The system of claim 17 further comprises:
the second hardware processor is configured to:
provide, via the display, a vision test to the user; and
create the vision profile based substantially on results of the vision test.

19. The system of claim 18, wherein the vision test comprises at least one or more of a version of an Ishihara test and a version of a Farnsworth Lantern test.

20. The system of any one of claims 17 to 19, wherein the first hardware processor is configured to:
determine, from the vision profile, the vision deficiency includes a colour vision deficiency; and
in response to determining the vision deficiency includes the colour vision deficiency, indicate the content transformation includes one of (i) changing at least one colour of the content to a different colour, (ii) replacing the at least one colour of the content with a pattern, and (iii) modifying the content.

21. The system of claim 20, wherein the first hardware processor is configured to:
identify, from the one or more contents, the content to be modified, the content including two neighbouring portions, each portion of the two neighbouring portions being associated with a respective first and second colour, the first colour being different from the second colour but the first colour being at least partially indistinguishable from the second colour by the user due to the vision deficiency.

22. The system of claim 21, wherein the first hardware processor is configured to:
identify a set of colours distinguishable by the user despite the vision deficiency; and
change the first colour to a colour from the set of colours, the colour being different from the second colour.

23. The system of claim 21, wherein the first hardware processor is configured to replace the first colour with a pattern.

24. The system of claim 17, wherein the severity level is selected from one of slightly deficient, moderately deficient, strongly deficient and absolutely deficient.

25. The system of claim 24, wherein the first hardware processor is configured to:

in response to determining the severity level is absolutely deficient, indicate the content transformation includes replacing at least one colour of the content with a pattern.

26. The system of claim 17, wherein the at least one property further comprises at least one of an expected access date of the content and an expected length of time required for transforming the content.

27. A computer-implemented method for assessing content for an electronic learning system during a content creation process, the content comprising at least course content for a course being provided to a group of students including a plurality of students, the method comprising:
receiving content data from a content creator, the content data being used to generate the content;
receiving from a database, one or more vision profiles associated with a corresponding one or more students of the plurality of students, at least one of the one or more vision profiles indicating a colour vision deficiency, the colour vision deficiency defined by a severity level of each of a red-blindness, a green-blindness and a blue-blindness;
identifying, from the group of students, any student impaired by the colour vision deficiency;
determining whether the content is deficient for at least one identified student impaired by the colour vision deficiency based on the one or more vision profiles, the content being deficient when at least two portions of the content are formed of a first colour and a second colour, respectively, the first colour being different from the second colour but, to at least one student of the at least one identified student impaired by the colour vision deficiency, the first colour being at least partially indistinguishable from the second colour,
in response to determining the content is deficient for at least one identified student impaired by the colour vision deficiency, causing a display to display an alert advising the content creator of the deficient content and causing the display to display one or more versions of the content as perceived by each of the at least one identified student for which the content is deficient and otherwise indicating the content is not deficient; and
in response to determining the content is deficient, receiving a content transformation for the deficient content.

28. The method of claim 27, wherein advising the content creator of the deficient content comprises:
providing a replacement content for the deficient content, the replacement content being formed of one or more colours distinguishable by the at least one individual impaired by the colour vision deficiency.

29. The method of claim 28, wherein the replacement content is selected from one of an alternative content and a modified content.

30. A system for assessing content for an electronic learning system, during a content creation process, the content comprising at least course content for a course being provided to a group of students including a plurality of students, the system comprising:
a database for storing one or more vision profiles associated with a corresponding one or more students of the plurality of students, at least one vision profile of the one or more vision profiles indicating a colour vision deficiency, the colour vision deficiency defined by a severity level of each of a red-blindness, a green-blindness and a blue-blindness;

an interface module for receiving content data from a content creator, the content data being used to generate the content; and
a hardware processor in electronic communication with the interface module and the database, the processor being configured to:
identify, from the group of students, any student impaired by the colour vision deficiency;
determine whether the content is deficient for at least one identified student impaired by the colour vision deficiency based on the one or more vision profiles, the content being deficient when at least two portions of the content are formed of a first colour and a second colour, respectively, the first colour being different from the second colour but, to at least one student of the at least one identified student impaired by the colour vision deficiency, the first colour being at least partially indistinguishable from the second colour;
in response to determining the content is deficient, for at least one identified student impaired by the colour vision deficiency, cause a display in communication with the processor to display an alert advise the content creator of the deficient content and cause the display to display one or more versions of the content as perceived by each of the at least one identified student for which the content is deficient and otherwise indicating the content is not deficient; and
in response to determining the content is deficient, receiving a content transformation for the deficient content.

31. The system of claim 30, wherein advising the content creator of the deficient content comprises:
providing a replacement content for the deficient content, the replacement content being formed of one or more colours distinguishable by the at least one individual impaired by the colour vision deficiency.

32. The system of claim 31, wherein the replacement content is selected from one of an alternative content and a modified content.

* * * * *